United States Patent [19]

Chien et al.

[11] Patent Number: 5,578,315
[45] Date of Patent: Nov. 26, 1996

[54] MUCOSAL ADHESIVE DEVICE FOR LONG-ACTING DELIVERY OF PHARMACEUTICAL COMBINATIONS IN ORAL CAVITY

[75] Inventors: Yie W. Chien, North Brunswick; Mona Nair, Highland Park, both of N.J.

[73] Assignee: Rutgers, The State University of New Jersey, New Brunswick, N.J.

[21] Appl. No.: 160,474

[22] Filed: Dec. 1, 1993

[51] Int. Cl.⁶ ........................................... A61K 9/20
[52] U.S. Cl. ................. 424/435; 424/434; 424/464; 424/465
[58] Field of Search .................... 424/434, 435, 424/464, 465

[56] References Cited

U.S. PATENT DOCUMENTS

| | | | |
|---|---|---|---|
| 4,226,848 | 10/1980 | Nagai et al. | 424/435 |
| 4,713,243 | 12/1987 | Schiraldie et al. | 424/435 |
| 4,740,365 | 4/1988 | Yukimatsu | 424/435 |
| 5,047,244 | 9/1991 | Sanvordeker | 424/435 |
| 5,081,157 | 1/1992 | Pomerantz | 514/781 |
| 5,081,158 | 1/1992 | Pomerantz | 514/781 |
| 5,112,620 | 5/1992 | Repka | 514/180 |
| 5,116,603 | 5/1992 | Friedman | 424/53 |
| 5,234,957 | 8/1993 | Mantelle | 514/772.6 |

FOREIGN PATENT DOCUMENTS

| | | |
|---|---|---|
| 0159604 | 10/1985 | European Pat. Off. |
| 0200508 | 12/1986 | European Pat. Off. |
| 0283434 | 9/1988 | European Pat. Off. |
| 0306454 | 3/1989 | European Pat. Off. |
| 0393007 | 10/1990 | European Pat. Off. |
| 0451433 | 10/1991 | European Pat. Off. |
| 5843915 | 3/1983 | Japan . |
| 62-178513 | 8/1987 | Japan . |
| 63-54318 | 3/1988 | Japan . |
| 63-160649 | 7/1988 | Japan . |
| 6450815 | 2/1989 | Japan . |
| 1279838 | 11/1989 | Japan . |
| 1267618 | 3/1972 | United Kingdom . |
| 2042888 | 10/1980 | United Kingdom . |

OTHER PUBLICATIONS

WO89/10740, Innovata Biomed Ltd, "Buccal Local Anaesthetic", Published Nov. 16, 1989.
WO92/00725, Farcon AG, "Liquid Oral Pharmaceutical Compositions Having Anti–Inflamatory Activity", Published Jan. 23, 1992.
WO92/17167, Biotech Australia, "Oral Delivery Systems For Microparticles", Published Oct. 15, 1992.
Drug Development And Industrial Pharmacy, 19(14), 1755–1808, 1993 "A New Transmucosal Therapeutic System:Overview Of Formulation Development And In–Vitro/In–Vivo Clinical Performance", Y. Nozaki, et al.
Eur J Clin Pharmacol (1992) 43: 137–140, "Comparison of Salivary Miconazole Concentrations After Adminstration of A Bioadhesive Slow–Release Buccal Tablet And An Oral Gel", S. Bouckaert, et al.
Journal of Pharmaceutical Sciences, vol. 79, No. 2, Feb. 1990, "Bioadhesive Lozenge For The Improved Delivery of Cetylpyridinium Chloride", Augusta Collins, et al.
Journal of Controlled Release, 6(1987) 353–360, "Buccal/Gingival Drug Delivery Systems", Nagal.

Primary Examiner—Carlos Azpuru
Attorney, Agent, or Firm—Schwegman, Lundberg, Woessner & Kluth, P.A.

[57] ABSTRACT

Mucosal adhesive devices are provided for use in the oral cavity for therapy against infections. The devices are dosage units which comprise a combination of antimicrobial agents such as antifungal agents and anti-inflammatory agents, optionally also a local anesthetic. The dosage units yield a gradual and relatively constant release of the pharmaceuticals over at least a 12-hour period.

8 Claims, 14 Drawing Sheets

BIADHESIVE STRENGTH OF THE TABLETS MADE WITH VARIOUS POLYMERS

| POLYMER | ADHESION FORCE[a] (gm) | WORK[a] (gm,cm) |
|---|---|---|
| SODIUM CARBOXYMETHYLCELLULOSE | 119.85(0.21) | 684.75(18.45) |
| CARBOPOL | 102.83(6.50) | 1343.00(250.74) |
| POLYETHYLENE OXIDE | 109.73(4.48) | 694.28(7.27) |
| POLYMETHYLVINYLETHER / MALEIC ANHY. | 10.97(0.57) | 42.89(2.62) |
| TRAGACANTH | 34.75(4.96) | 307.46(26.33) |

[a] MEAN OF 3 DETERMINATIONS (± ONE STANDARD DEVIATION)

FIG. 6

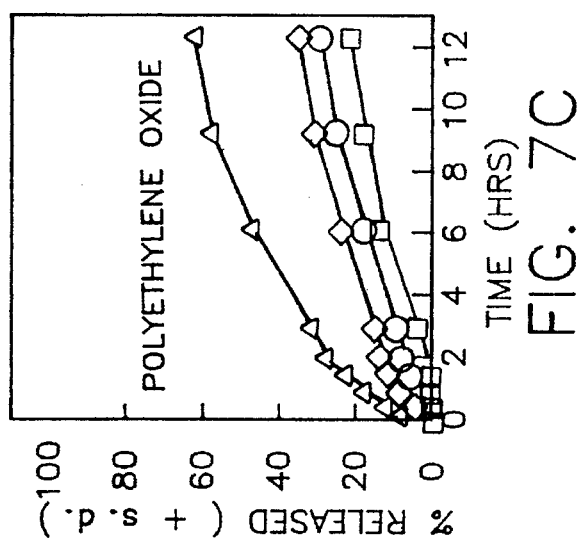
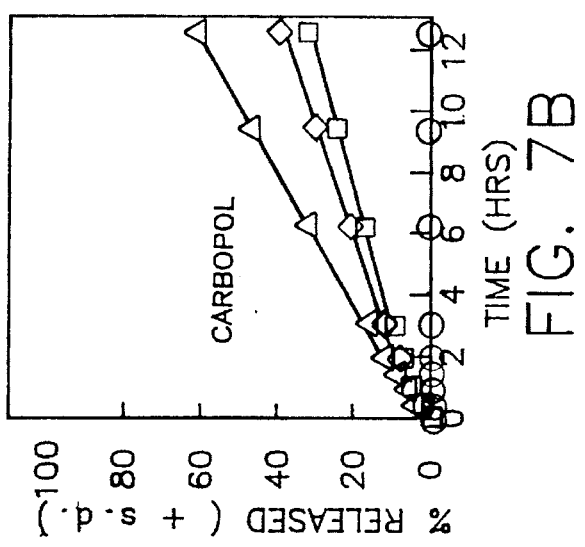
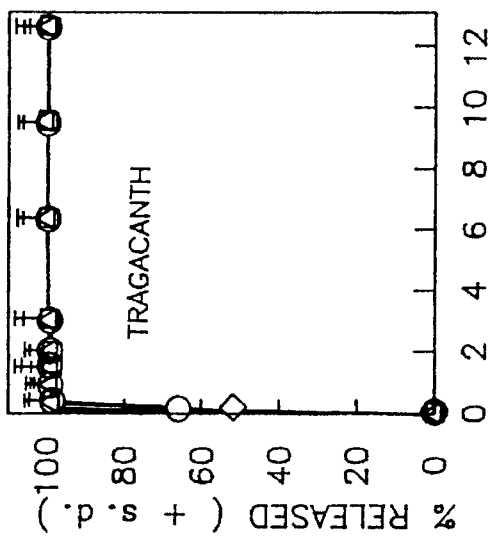
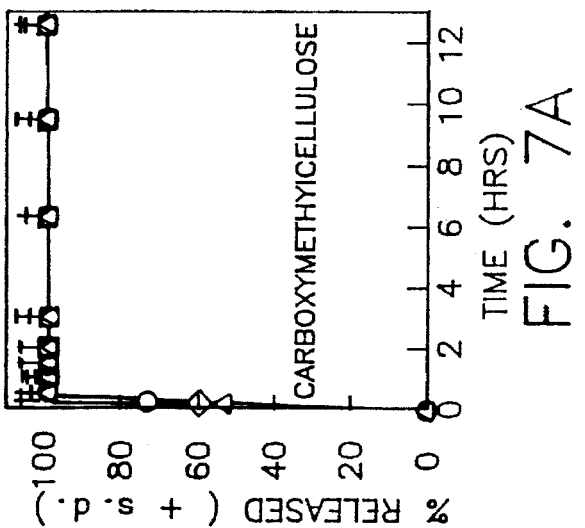
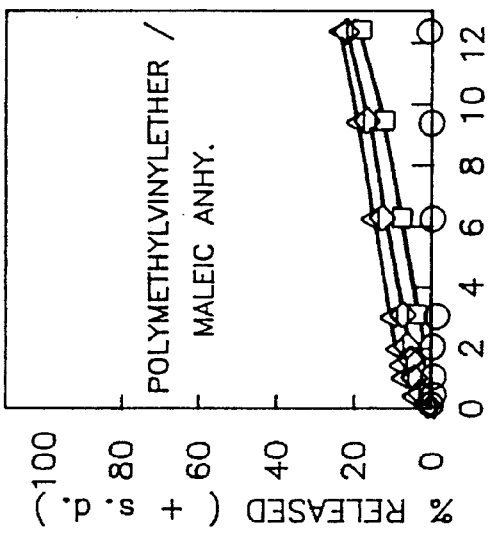

CARBOXYMETHYLCELLULOSE:POLYETHYLENE OXIDE ( ○ 75:25, □ 50:50, ◇ 25,75)

CARBOXYMETHYLCELLULOSE:POLYETHYLENE OXIDE (○ 80:20, □ 85:15, ◇ 90:10 & 95:5)

● BUCCAL-BENZOCAINE
■ BUCCAL-HYDROCORTISONE
○ ALVEOLAR-BENZOCAINE
□ ALVEOLAR-HYDROCORTISONE 5,578,315

MUCOSAL ADHESIVE DEVICE FOR LONG-ACTING DELIVERY OF PHARMACEUTICAL COMBINATIONS IN ORAL CAVITY

TECHNICAL FIELD

This invention relates to a novel drug delivery device designed for controlled delivery of a combination of pharmnaceuticals to the oral cavity for the treatment of oral tissue infections. More particularly, it is directed to a dosage unit which is applied to the mucosal tissues of tile oral cavity in the form of a dosage unit with a mucoadhesive surface with or without a protective backing layer. A combination of antimicrobial agent, anti-inflammatory agent, and optionally a local anesthetic are dispersed in the mucoadhesive matrix.

BACKGROUND ART

Certain dosage forms are available for pharmaceutical delivery in the oral cavity. Many of these dosage forms have tile disadvantage of rapid initial release of pharmaceutical followed by a rapid decline in the release rate of the pharmaceutical to a sub-therapeutic level. The dosage forms known have taken the form of a lozenge in which pharmaceuticals of several types have been incorporated into the lozenge. Also, the known forms have included a form which has a backing layer on which is applied a mucoadhesive layer, and secondly, a tablet form which is fabricated having one or more mucoadhesive polymers and also having one or more pharmaceuticals interspersed into the structure of the tablet. These latter forms can be applied to the mucosal tissue of the oral cavity.

The pharmaceutical can be delivered to a local area of the oral cavity which is infected, for example, by a common cold sore, candidiasis or other conditions.

Other forms can provide the release of pharmaceutical for general therapy in the oral cavity or for systemic absorption. However, often they contain a single therapeutic class of pharmaceutical.

It would be highly desired to have mucoadhesive dosage frowns which provide the release of the combination of pharmnaceuticals at a relatively constant rate over at least a 12-hour period. Of special importance would be such a mucoadhesive dosage form which treats local infective conditions in the oral cavity.

SUMMARY OF INVENTION

By this invention is provided mucosal adhesive dosage units for administration of pharmaceuticals simultaneously at controlled rates over a period of, for example, at least 12 hours. It is desired that the dosage unit provided by this invention provide a combination of one or more antimicrobial agents, one or more anti-inflammatory agents and optionally one or more local anesthetics, to be applied to and to adhere to the mucosal tissue of the oral cavity. It is desired that the dosage unit is adapted to treat local oral tissue infections.

The dosage units can be applied at or near the site of the local infection to enable the dosage units to treat the local infection of the oral cavity.

Localized infections, like common oral sores, as well as widely-spread infections, like candidiasis, and periodontal diseases, like chronic gingivitis, can be treated with the dosage units of this invention.

It has been found that for the substantially constant release of pharmaceuticals over a period of at least 12 hours, that the antimicrobial agent can desirably be an antifungal pharmaceutical, such as chlorhexidine or clotrimazole, for therapy against candidiasis infection. Other agents having an antifungal activity can be used instead of those named so long as the long term therapy and relatively constant rate of release are desired from the therapeutic points of view.

Anti-inflammatory pharmaceuticals presently desirable for use include hydrocortisone. Other anti-inflammatory agents can be used so long as they complement the therapeutic activities of antifungal agents or other antimicrobial agents over a period of at least 12 hours and provide effective anti-inflammatory action.

A suitable local anesthetic has been found to be benzocaine. Other local anesthetics can be used as long as they provide the desired long-term local analgesic effect.

The dosage form can be in the form of a dosage unit with a backing layer and adhered thereto a mucoadhesive polymer layer, which adheres to the mucosal tissue of the oral cavity. Often it is desired to use a combination of mucoadhesive polymers and other materials in order to provide an effective dosage unit. Alternatively, the dosage unit can be in the form of a tablet which contains an effective amount of one or more mucoadhesive materials, which can be also adhered to the mucosal tissue of the oral cavity. The combination of pharmaceuticals is uniformly dispersed in the tablet.

BRIEF DESCRIPTION OF THE DRAWINGS

FIG. 6 is a table showing bioahdesive strength of tablets made with various mucoadhesive polymers.

FIGS. 7-A, B, C, D and E show percent released (+s.d.) of the named pharmaceuticals using the named mucoadhesive materials vs. time in hours.

DETAILED DESCRIPTION OF THE INVENTION AND THE PREFERRED EMBODIMENTS

Figure 1:
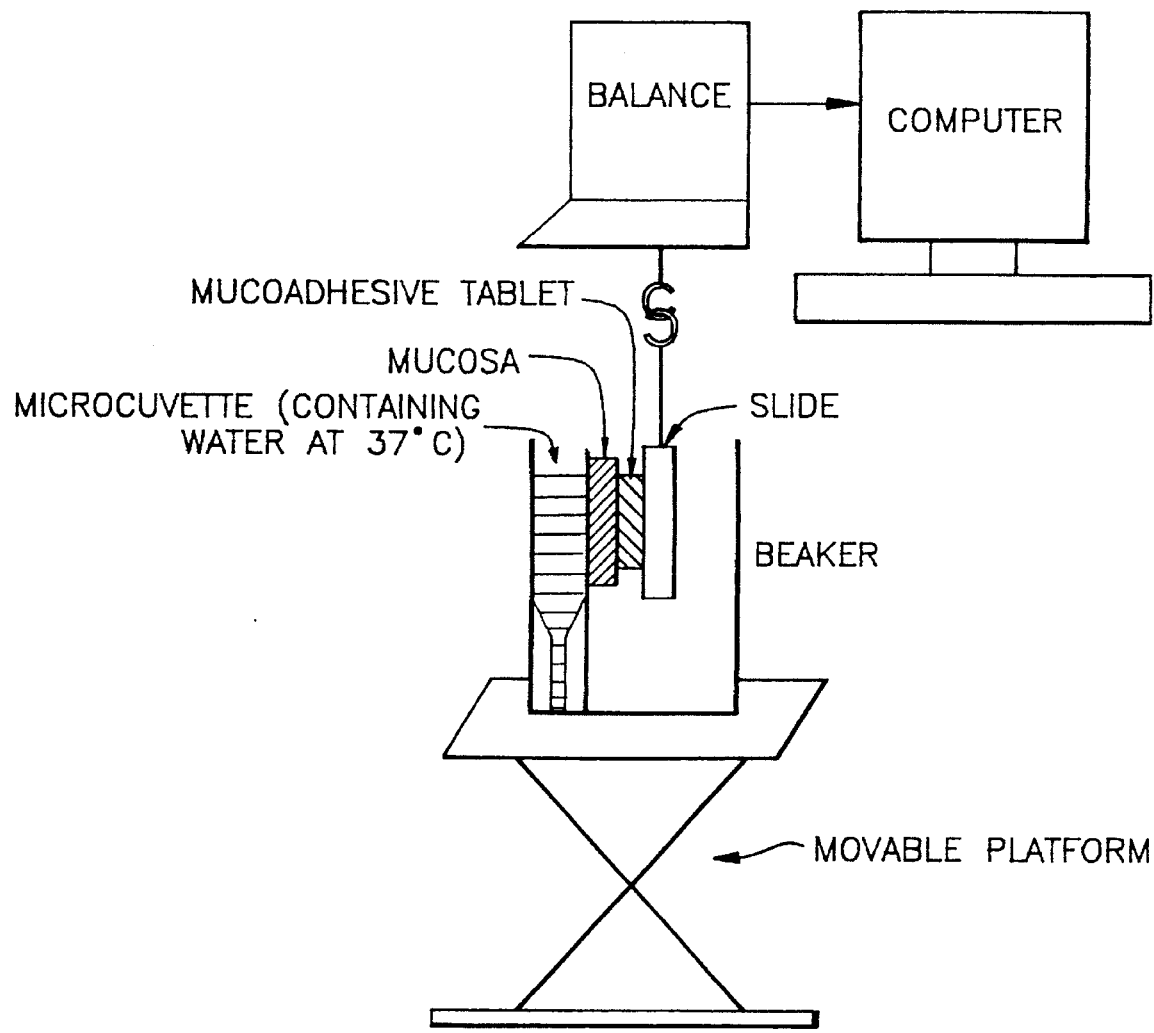
FIG. 1 shows the system used for measurement of the adhesive strength of the dosage units.

As mentioned above, the mucosal adhesive dosage units of this invention are of two forms. The first form utilizes a protective backing layer, which can be any backing layer material which is compatible with the tissues of the oral cavity and with the pharmaceuticals of the dosage unit. Suitable backing layer materials are sold under the designation Scotchpack, by 3M Corporation, St. Paul, Minn. To the backing layer is coated a composition comprising mucoadhesive polymer(s) in admixture with the pharmaceuticals, plasticizer if desired, and other materials.

A suitable means of preparing the mucoadhesive composition can involve a first step using the mucoadhesive polymer in a 1 percent by weight amount based on the final mucosal adhesive pharmaceutical composition. The polymer is dispersed in equal amount of a plasticizer, suitably glycerol, in the amount of 1 percent by weight of the final composition.

It has been found suitable to make up stock solutions of the pharmaceuticals utilized. It has been found suitable to utilize a lower alkanol as the solvent to provide stock solutions of certain pharmaceuticals found useful in this invention. For example, 2 mg/gm of polymer stock solution is found suitable with regard to benzocaine and hydrocortisone and 1 mg/gm of the mucoadhesive polymer/pharmaceutical composition when using antifungal agents chlorhexidine and clotrimazole.

After forming the mixture of polymer, plasticizer and pharmaceutical solution, in order to form the required final concentration water is added and mixed to form the resulting dispersion and to bring the weight up to the desired 100%.

The final polymer/pharmaceutical mixture as formed is then cast on a selected backing layer to a thickness which is suitable in the particular instance. It has been found that a wet thickness of about 100 microns is ordinarily satisfactory. It has been found suitable to use a standard coating machine in the coating step. Specifically, it has been found suitable in preparation, on a laboratory scale, to use a coating machine provided by Wamer-Mathis of Zurich, Switzerland.

After coating the backing, the coating is dried and the dosage units can be cut into any suitable size and shape. It has been found convenient ordinarily to form circular patches having a diameter of about 10 millimeters. Suitable diameter can range from 5 to 15 millimeters, depending upon the therapeutically effective dose of the pharmaceutical, the effective area to be treated, the quantity of the pharmaceutical to be administered, and other factors. The shape and the size of the patch, of course, must be in conformity to the area of the oral cavity to which the patch is applied.

The patch can be assayed for concentration of the pharmaceuticals and its release or its adhesion strength, pharmaceutical release rates and for other purposes as desired. The dosage units foraged can be varied as desired.

Various mucoadhesive polymers can be used, depending upon desired release rates of pharmaceutical, biocompatibility, adhesive strength required for long-term application and other factors. The mucoadhesive which is used can be selected from one or more mucoadhesives as sodium carboxymethyl cellulose, polyacrylic acid, such as sold under the designation Carbopol or polycarbophil, polyvinylpyrrolidone, polyethylene oxide, polyvinylmethylether/maleic anhydride dopolymer, methyl cellulose, methylethyl cellulose, polyacrylamide, polyethyleneglycol, polyvinylalcohol, polyhydroxypropyl cellulose, polyhydroxyethylmethacrylate, and other suitable mucoadhesive polymers.

Various other agents can be added so long as they do not have a toxic effect and are compatible with oral mucosal and the other ingredients of the mucoadhesive polymer layer, such as certain salts which can modify the solubility, release rates and other factors. Such salts can include disodium hydrogen orthophosphate, potassium dihydrogen orthophosphate, sodium chloride and other agents.

In the second dosage form, which is the tablet form, many of the same ingredients can be used in the preparation of the oral mucoadhesive tablet. In general, the tablets can be formed by mixing the mucoadhesive polymers with the desired pharmaceutical agents required in the dosage unit and a required amount of lubricant and glidant, such as talc. Satisfactory talc can be obtained from Fisher Scientific (Fair Lawn, N.J.). A suitable amount of the lubricant and glidant, if talc is used for this propose, can be 5% by weight based on the final tablet mixture. This amount can be increased or decreased so long as there is an adequate amount for formation of the desired tablet. The total quantity of pharmaceutical in the final tablet can often be suitably in the general range of 5–10% on a weight basis. It will be evident that this quantity can be varied, dependent upon the desired dosage of the particular pharmaceuticals used and the desired release rate and other factors. Assuming that there are four therapeutic agents and that talc is used as a lubricant and glidant, there will be a total of 20–40% based on the weight of the final tablet mixture of these ingredients. Under these circumstances, about 75–55% by weight of mucoadhesive polymer is added. The combination then is thoroughly mixed.

A suitable tableting machine for making the tablets on a laboratory scale is a Carver Laboratory Press sold by Fred S. Carver, (Menomonee Falls, Wis.), or a tablet press. The diameter of the die cavity can vary, but it has been found that a cavity having 8 millimeters in diameter and holding 100 mg of the tablet mixture is suitable. Using this molding machine, a compression force of about 10,000–11,000 lbs. (approximately 5 metric tons) for 5 seconds has been found suitable for forming tablets, which represent the tablet dosage forms of this invention.

The tablets can be assayed and evaluated for various factors. For example, they can be assayed for uniformity of pharmaceutical content, the physical characteristics of the tablets, the bioadhesive strength of the tablets and the like, following the test and evaluating procedures as hereinafter described or which will be evident to those having skill in this art. There are various oral tissue infections to which the dosage units of this invention are directed:

TABLE I

Oral Tissue Infections

| A. | Common Oral Sores: | Canker sores |
| --- | --- | --- |
| | | Cold sores |
| B. | Common Oral Infections: | Candidiasis |
| | | Dentopyogenic infections |
| | | Oralcancer |
| C. | Peritodontal Disease: | Acute necrotizing ulcerative gingivitis |
| | | Chronic gingivitis |
| | | Pregnancy gingivitis |
| | | Periodontitis |

TABLE II

Recurrent Oral Tissue Infections

Common Oral Sores

Canker sores (aphthous ulcers)

Affect 20–50% of Americans
May result from a hypersensitivity to antigenic components of *streptococcus sanguis*.
Multiple lesions on any nonkeratinized mucosal surface, very painful and recurrent.

Cold sores (*Herpes labialis*)

Caused by *herpes simplex* Type I virus.
Commonly occur on the lip or bordering area.
Recurrent, often repeat in the same location.
Painful and cosmetically objectionable.
Transmissible by direct contact.

Common Oral Infections

Candidiasis

Caused by *candida albicans* (normal flora in oral cavity GI tract).
Appears in debilitated patents and patients taking a variety of drugs which depress defense mechanism.

Dentopyogenic Infections

Pus-producing infection around a tooth or its supporting structures.
Severity ranges from small, well-localized abscesses to a diffuse, rapidly spreading cellulitis or osteomyelitis with high morbidity and mortality.

TABLE III

Current Methods for Treatment of Common Oral Sores by Nonprescription Drugs

| Treatment Goals | Non-prescription Product |
| --- | --- |
| Canker Sore: | |
| 1) To afford pain relief | Local anesthetic pastes or |
| 2) To control discomfort | gels, e.g., benzocaine (5–20%) |
| 3) To promote healing | |
| Cold Sore: | |
| 1) To control discomfort | Local anesthetics in non-drying |
| 2) To promote healing | base |
| 3) To prevent drying fissuring and secondary bacterial infection | Topical oral protectants, e.g. Orabase |
| | Topical antibiotic ointments, e.g., bacitracin/neomycin |

The pharmnaceuticals which can be selected come within the following groups:

1. Antimicrobial agents can be selected from the following or other suitable ones:

Azoles: Clotrimazole, Miconazole, Ketoconazole, Econazole, Terconazole,

Itraconazole, Fluconazole, Sertaconazole, Saperconazole, Flutrimazole;

Polyenes: Amphotericin A & B, Nystatin, Candicidin, Natamycin

Bisguanides: Chlorhexidine

Pyrimidine derivatives: Flucytosine

Quarternary ammonium compounds: Cetylpyridinium Cl, Benzalkonium

Cl, Cetrimide

Morpholine derivatives: Amorolphine

Allylamines: Naftifine, Terbinafine

Polyether derivatives: Ganbieric acids A & B

Miscellaneous: Griseofulvin, Tolnaftate, Benzoic acid, Salycilic acid, Crystal violet, Potassium chloride, Povidone iodine 2. Anti-inflammatory, can be selected from the following compounds or other suitable ones:

NSAIDs: Pyridoxine HCl, Diclofenac sodium, Naproxen, Ibuprofen, Ketoprofen,

Indomethacin, Mefenamic acid, Phenazone, Phenylbutazone,

Oxyphenbutazone, Methyl salicylate, Salicylic acid, Salicylamide

Corticosteroids: Hydrocortisone, Cortisone, Beclomethasone,

Betamethasone, Dexamethasone, Paramethasone, Prednisolone, Prednisone,

Methylprednisolone, Triamcinolone, Fluocinolone, Halcinonide, Amcinonide (and salts thereof)

3. Local anesthetic pharmaceuticals can be selected from the following or other suitable ones:

Ester type: Benzocaine, Amethocaine, Cocaine, Procaine

Amide type: Bupivacaine, Cinchocaine, Etidocaine, Lignocaine (lidocaine),

Mepivacaine, Prilocaine

Miscellaneous: Benzyl alcohol, Chlorbutol, Menthol, Phenol

In forming the dosage units of this invention, combinations of mucoadhesive polymers can be used at times to advantage. Also, various combinations of the pharmaceuticals can be utilized.

It is highly desired that the rate of release of the pharmaceuticals in the dosage units extend on a substantially steady rate for at least 12 hours.

Certain combinations of the pharmaceuticals, for example, antimicrobial agents, have been found to provide a synergistic type of activity. It has been found that combinations of chlorhexidine and clotrimazole have provided a synergistic effect in a number of oral diseases, such as oral cancer, gingivitis, plaque and dental somatosis, for example, if an equal amount by weight of each is used. The ratio of the amounts of the two pharmaceuticals can be varied to provide synergistic effect, for example, within the range of 20–80 percent of each.

Generally speaking, the two different types of dosage units of this invention each have a special type of use. The dosage unit having the backing is especially useful for localized, uni-directional delivery of drugs. It is useful for treatment, for example, of isolated lesions and for such local activity. The bioadhesive tablet is useful for more general treannent of the oral cavity. It is useful for treatment of oral candidiasis that typically affects the entire oral mucosal surface and is not localized to small areas to which the dosage unit having a backing would be inapplicable.

Various methods and tests are employed in carrying out the invention, including the following:

Polymer Swelling

The degree of polymer swelling is determined by adding 25 ml of isotonic phosphate buffer (pH 6) to the respective polymer (0.5 gms) in a 25 ml measuring cylinder. The cylinders are covered to prevent loss of water due to evaporation and kept in an oven at 37° C. The degree of swelling is read directly from the cylinder at regular intervals until no further polymer hydration occurs.

Viscosity of Polymer Solutions

The viscosity of the polymer solutions are determined using a cone-plate viscometer (Brookefield Ins./Stoughton, Mass.). Polymer solutions are made by dispersing 1.5% w/w of the polymer in methanol (49.25% w/w, containing the drugs), and adding to this solution 49.25% w/w water. The resulting mucilage is stirred and 0.5 ml placed on the plate of the viscometer. The viscometer is then run at 10 rpm and the % reading obtained. In case of polymethylvinyl ether/maleic anhydride, a speed of 100 rpm is required to obtain a reading.

Content Uniformity of Patches

Each patch is immersed in a test tube containing 3.5 ml of methanol or water, as required. The tubes are sealed and shaken in a wrist-action shaker (Burrell Corp./Pittsburgh, Pa.) for 6 hours. The amount of drug is determined by HPLC to quantitate the loading of drugs in each patch.

Drug Release from Patches

The release kinetics of the drugs from the patches are studied in the Valia-Chien permeation cells at 37° C. The patches are fixed between the two half-cells with the backing membrane facing the donor half-cell and the drug-adhesive layer facing the receptor half-cell. Isotonic phosphate buffer (pH 6.8) containing 20% PEG 400 (3.5 ml), to ensure that sink conditions are maintained for the released drugs, serves as the receptor medium. The surface area of the patch exposed for drug release is 0.64 cm$^2$.

The release studies are carried out for a duration of 4 hours and samples (200 µl each for both HPLC and growth inhibition assays) are withdrawn at present time intervals.

Growth Inhibition Assay

Samples (100 µl each) of the receptor solution (frown the release studies) are added to a 24-well microliter plate (3 ml/well). To each well 0.9 ml of sterile RPMI 1640 medium and 100 µl of the inoculum is added. The initial amount of organism in the suspension at zero time is determined by similarly adding 100 µl of the inoculum to 1 ml of the medium devoid of any drug. The plates are incubated at 35° C. for 24 hours and the growth of organisms is determined spectrophotometrically, using disposable micro-cuvettes (Fisher Scientific), at 530 nm. The growth profile is plotted and correlated to the release of the antimicrobial drugs determined by HPLC assay. Care is taken to avoid contamination of the microtiter plates.

Content Uniformity of Tablets

Tablets, prepared as described above, are each crushed in a mortar with a pestle. Aliquots of the crushed tablets are weighed and the required amount of methanol is added to the powder to extract the drugs. The suspension is shaken in a wrist-action shaker (Burrell Corp./Pittsburgh, Pa.) for 6 hours. Samples are withdrawn, diluted as required, and the concentration of each drug is determined by HPLC.

Physical Characteristics of Tablets

Tablet thickness is determined using a micrometer and tablet hardness is measured using a Tablet Hardness Analyzer (VK 2000) (Vankel Industries Inc./Edison, N.J.).

Bioadhesive Strength of Tablets

The bioadhesive strength of the tablets prepared from various polymers is estimated by the adhesion force and the work of adhesion required to separate the tablet from a mucosal membrane specimen, with mucin solution (0.25%) serving as the interstitial medium.

The membrane specimen is adhered to a disposable microcuvette which in turn is clamped to the inside wall of a beaker kept on an electronic jack. The microcuvette is filled with water at 37° C. The tablet is adhered on a plexiglass slide using cyanoacrylate glue. The slide is hung from the underside of a semi-microbalance and is brought in contact with the vertically placed membrane, which is previously wetted with 0.25% mucin solution, such that the two are in exact parallel position. The membrane specimen and the tablet are in contact for 5 minutes, subsequent to which the jack is lowered at a constant rate (0.225 ram/sec.), and the adhesion force vs. time profile is monitored on a computer interfaced with the balance. The maximum adhesion force and the area under the force/time curve (work of adhesion-shear) is determined for each polymer. This analytical device and procedure is illustrated in FIG. 1.

Pharmaceutical Release from Tablets

Pharmaceutical release from the tablets is determined using a dissolution apparatus (Vankel Industries Inc./Edison, N.J.). Isotonic phosphate buffer containing 40% PEG 400 is used as the dissolution medium. PEG is used in order to maintain sink conditions for the released pharmaceuticals. 200 ml of the dissolution medium is used and dissolution studies are performed at 37° C. with paddle rotating at 50 rpm. Samples (100 µl each) are withdrawn at preset time intervals for a period of 12 hours, and the amount of pharmaceutical in the samples is determined by HPLC.

Transmucosal Permeation

Buccal and alveolar mucosae are surgically excised from freshly sacrificed pigs (Dealaman Enterprises/Warren, N.J.) and the underlying muscle and connective tissue are removed. The buccal mucosa is mounted on one half-cell of each Valia-Chien permeation cell, with its serosal surface facing the receptor solution compartment. The alveolar mucosa is secured on the inner side of a mucoadhesive tablet-holding device, and the tablet is then adhered directly onto the alveolar mucosa surface. The device is then clamped between the two halfcells, such that the other side of the tablet is in close contact with the buccal mucosa. The exposed surface for buccal membrane permeation is 0.64 cm$^2$, and for the alveolar membrane, permeation is 0.03 cm$^2$. All aliquot (100 µl) of the receptor medium is added into the device for dissolution of the tablet. Isotonic phosphate buffer (pH 6.8, 3.5 ml) containing 40% PEG 400 is added, as the receptor medium, in the solution compartment of both half-cells, and the permeation experiment is carried out at 37° C. for a period of 24 hours. Samples (50 µl each) are withdrawn at preset time intervals and analyzed by HPLC.

Analytical Method

A method for the analysis of chlorhexidine [15] is modified to permit simultaneous detection of all four drugs. Quantition of the pharmaceuticals is done by injecting samples (10 µl each) into an HP 1050 system (Hewlett Packard/Avondale, Pa.). An ODS-Hypersil column (5 µm, 100 mm×2.1 mm; Hewlett Packard) is used and gradient elution is carried out, so all the drugs can be quantitated. The mobile phase comprises acetonitrile and acetate buffer with the gradient varying from 90% and 10% to 40% and 60% over a period of 20 minutes.

The acetate buffer is made by dissolving sodium acetate (0.2% w/w) in water and adding triethylamine (0.4% w/w) to it. The pH of the buffer is then adjusted to 5 with glacial acetic acid.

Figure 2:
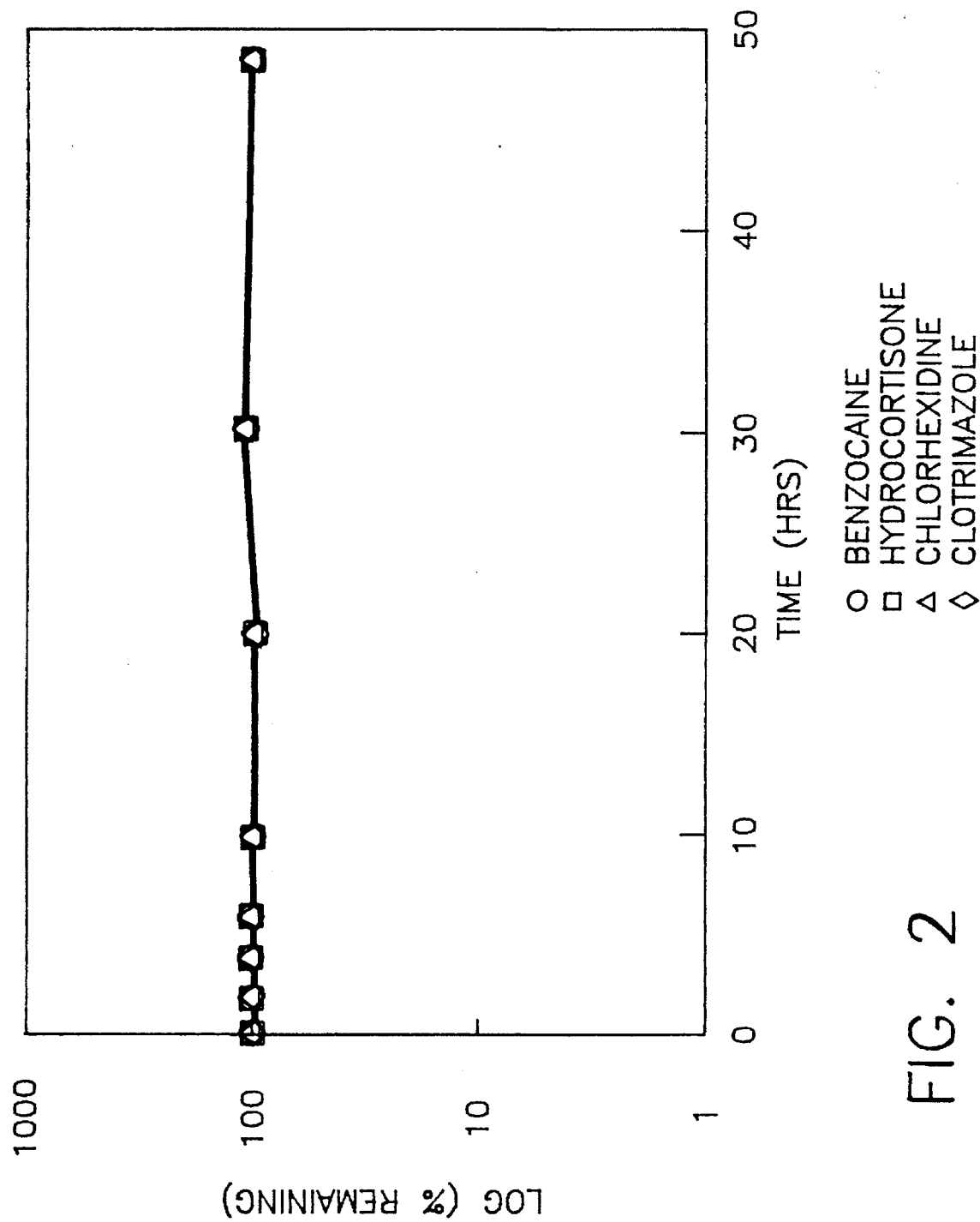
FIG. 2 is a graph showing the log of the percent of the remaining pharmaceutical in the dosage unit vs. time (hours).

The HPLC profile for the mixture of pharmaceuticals (25 µg/ml each), as analyzed by the above method, is shown in FIG. 2. The elution sequence follows the order benzocaine, succeeded by hydrocortisone, then chlorhexidine and finally clotrimazole. The limit of detection for benzocaine and hydrocortisone is <1µg/ml and that for chlorhexidine and clotrimazole is approximately 2 µg/ml.

Solubility

For use of clotrimazole, solubility in phosphate buffer is an issue and therefore, 20% and 40% PEG 400 are added to the phosphate buffer and the solubility is determined. The solubility of clotrimazole in isotonic phosphate buffer (pH 6.8) containing 20% PEG is around 60 µg/ml while in phosphate buffer containing 40% PEG the solubility is around 430 µg/ml.

Stability

Figure 3:
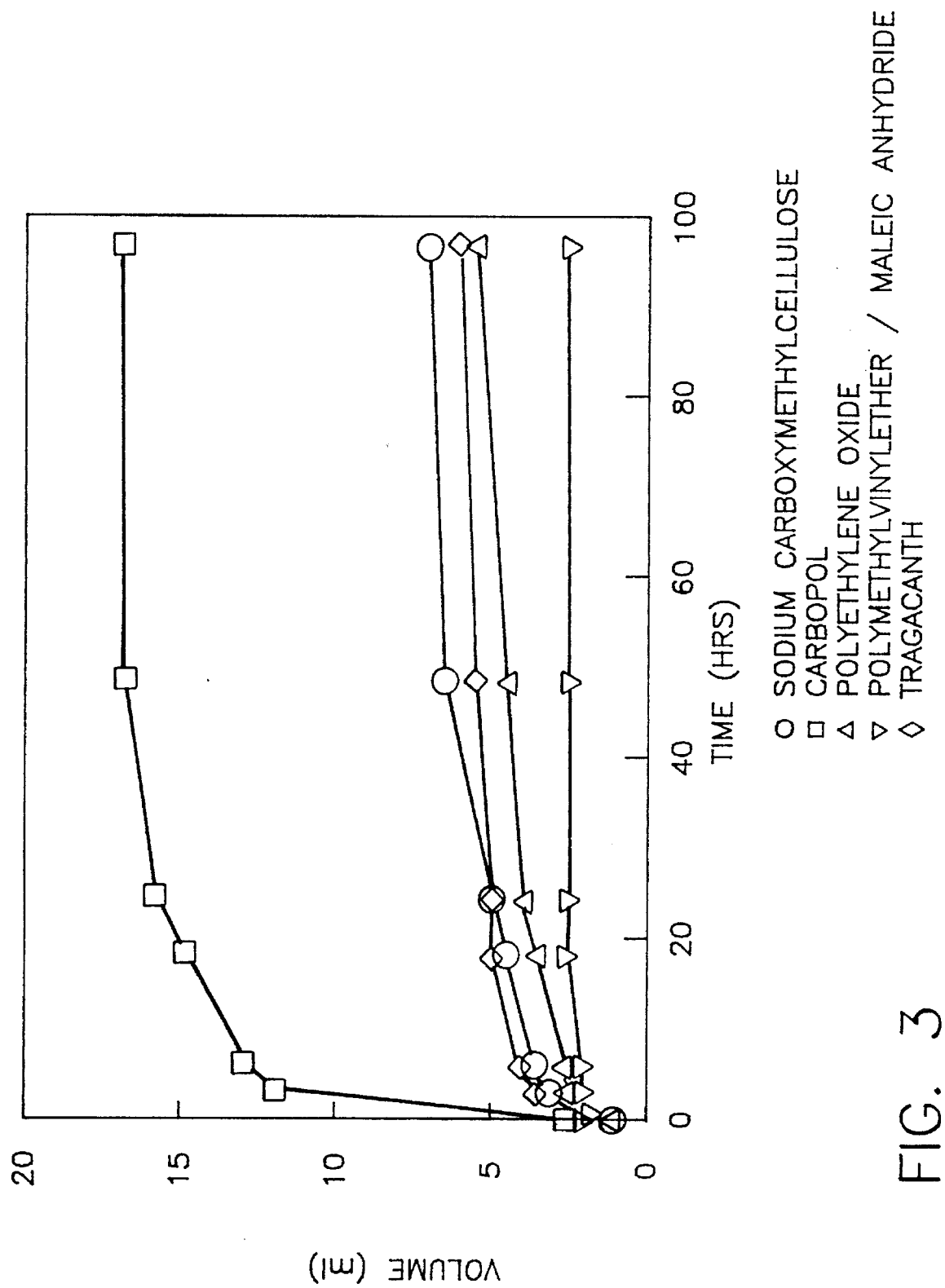
FIG. 3 is a graph showing the volume (ml) vs. time (hours) profile of various mucoadhesive materials used in making the dosage units.
Figure 4:
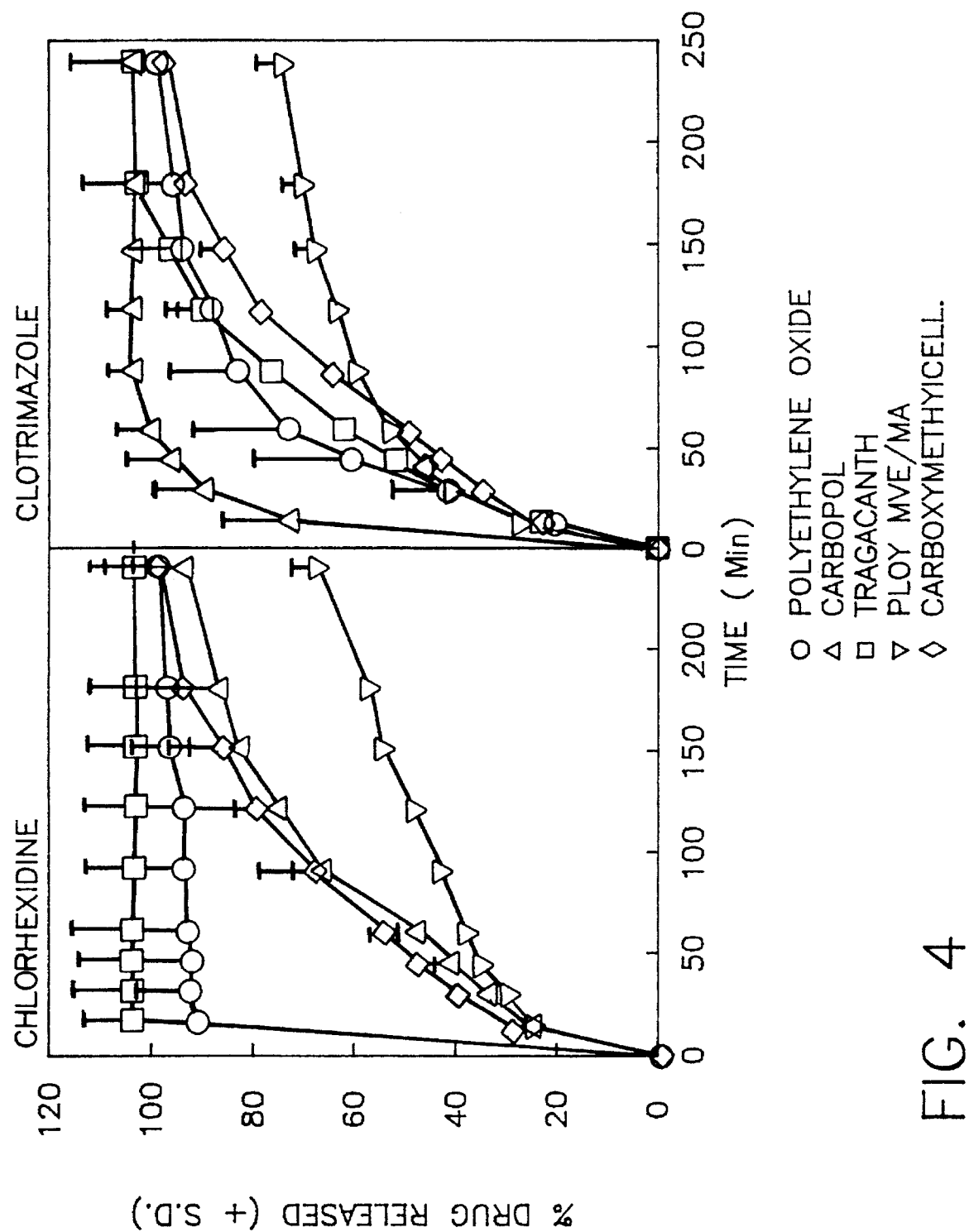
FIG. 4 is a graph showing the percent drug released (+s.d.) vs. time in minutes for chlorhexidine and clotrimazole using different mucoadhesive materials in the preparation of the dosage units.
Figure 5:
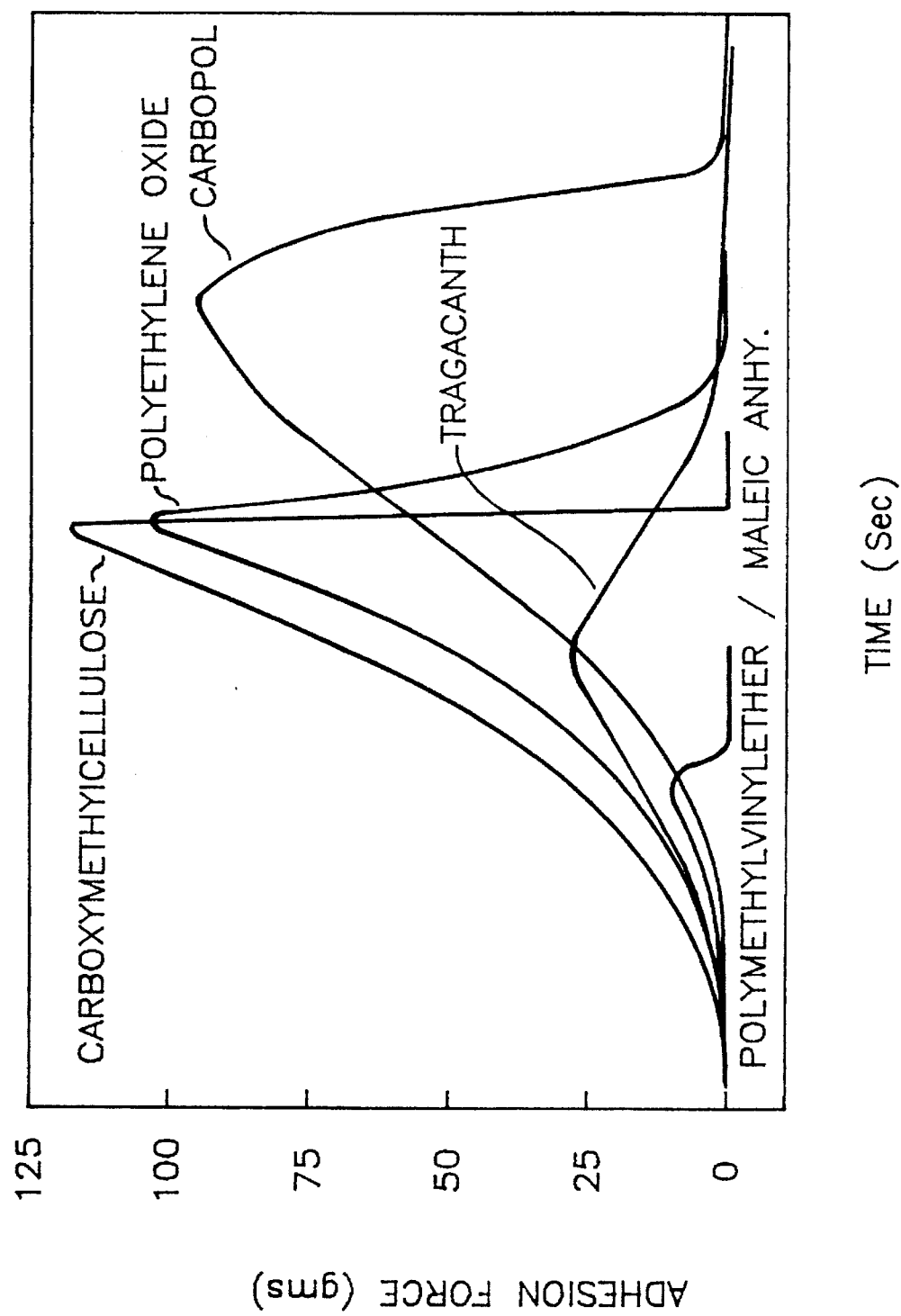
FIG. 5 is a graph showing the adhesion force (gms) vs. time (in seconds) for dosage units using different mucoadhesive materials in the preparation thereof.
Figure 8B:
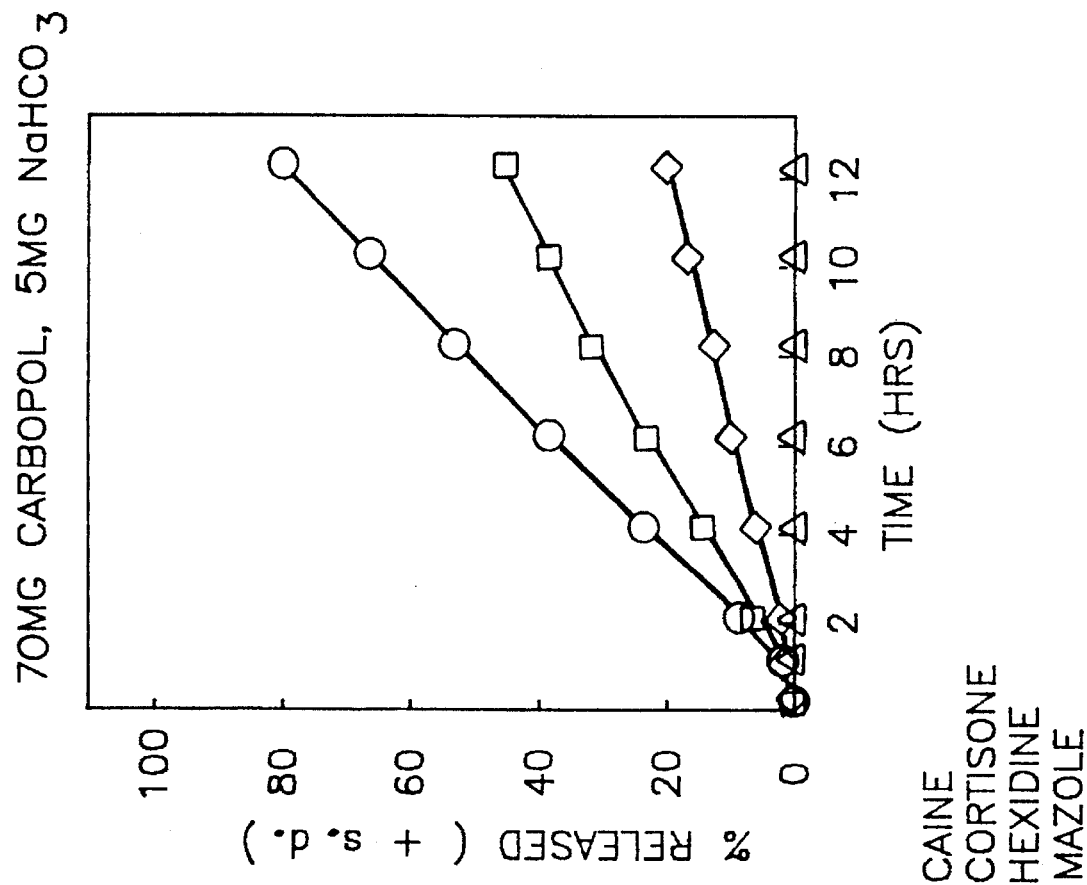
FIGS. 8-A and 8-B show the amount percent released (+s.d.) of the named pharmaceuticals from Carbopol adehsive polymer having either zero amount of sodium bicarbonate per 70 mg of Carbopol polymer vs. time (in hours).
Figure 8A:
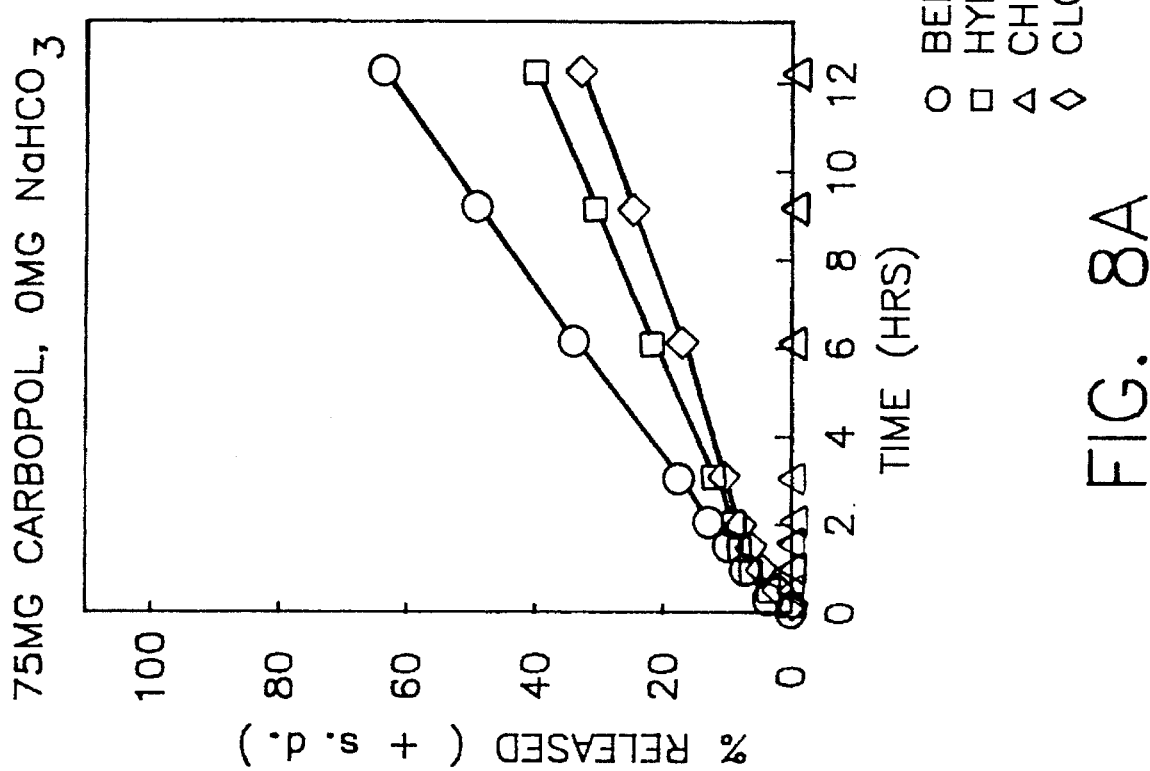
Figure 9:
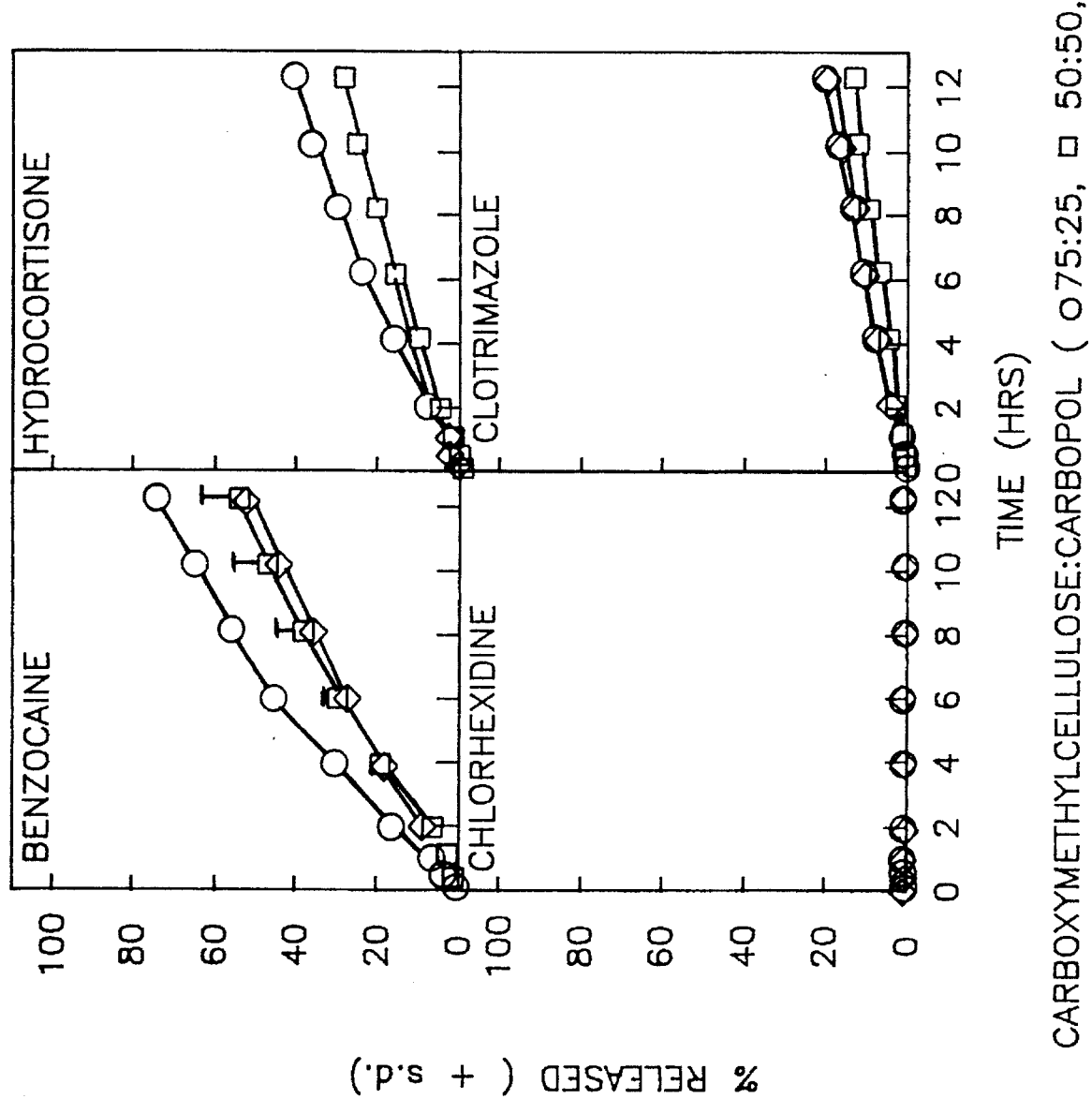
FIG. 9 shows percent released of 4 different pharmaceuticals (+s.d.) vs. time (in hours) for three different ratios of carboxymethyl cellulose:Carbopol polymer.
Figure 10:
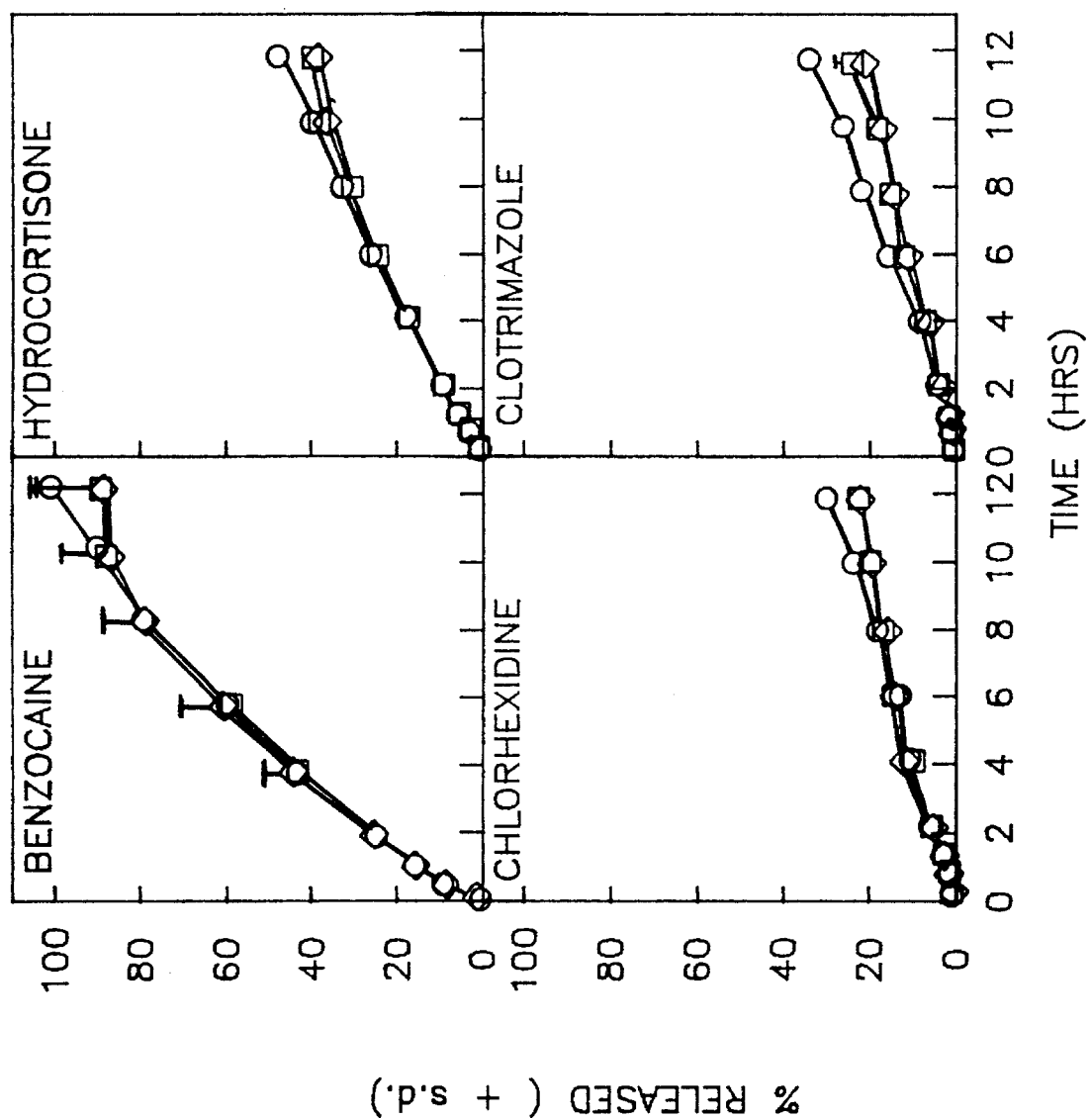
FIG. 10 are graphs showing percent released (+s.d.) for four different pharmaceuticals vs. time (in hours) using three different combinations of carboxymethiyl cellulose:polyethylene oxide.
Figure 11:
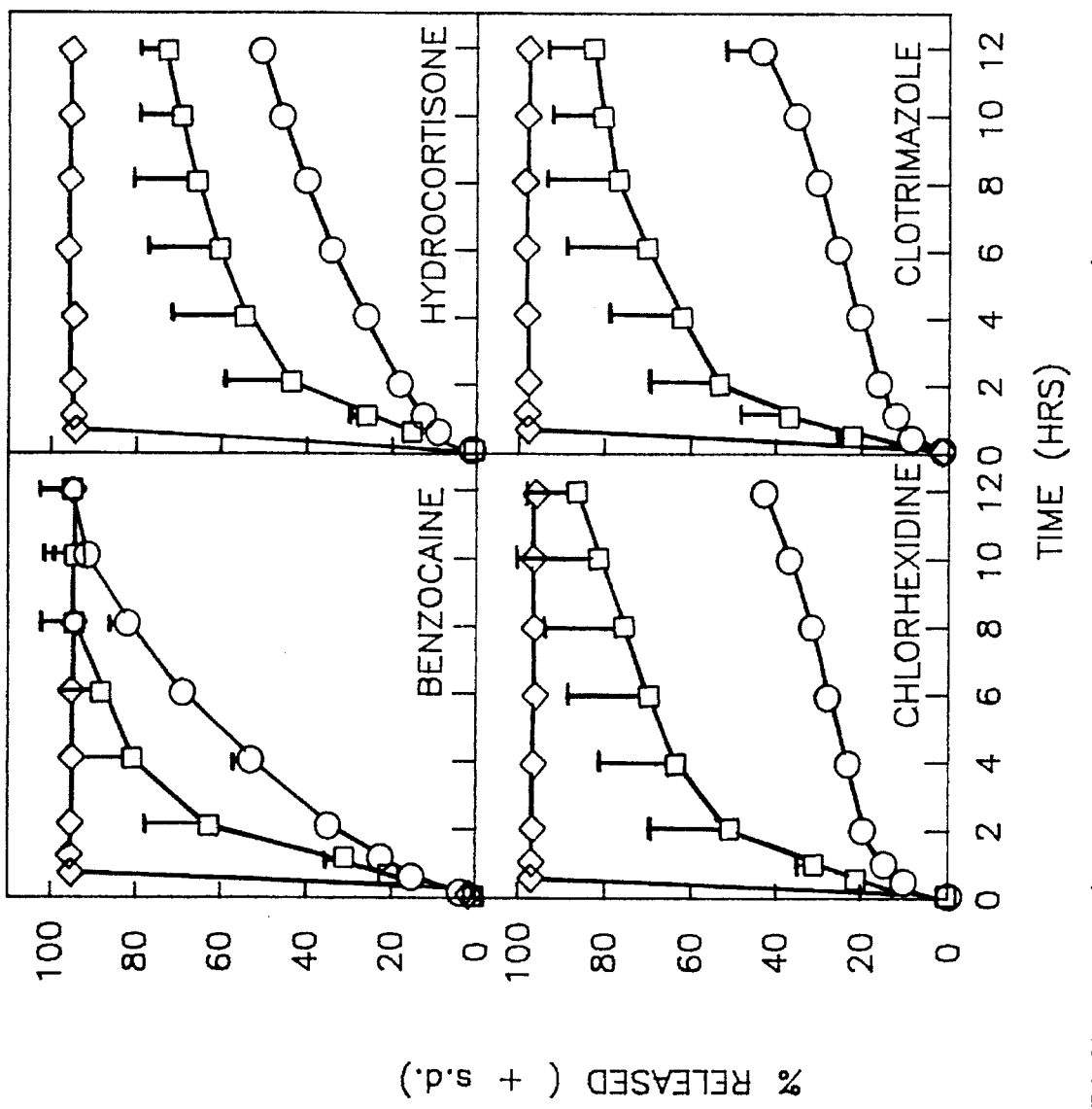
FIG. 11 are graphs showing percent released (+s.d.) of four pharmnaceuticals vs. time (in hours) using four higher ratios of carboxymethyl cellulose:polyethylene oxide.
Figure 12:
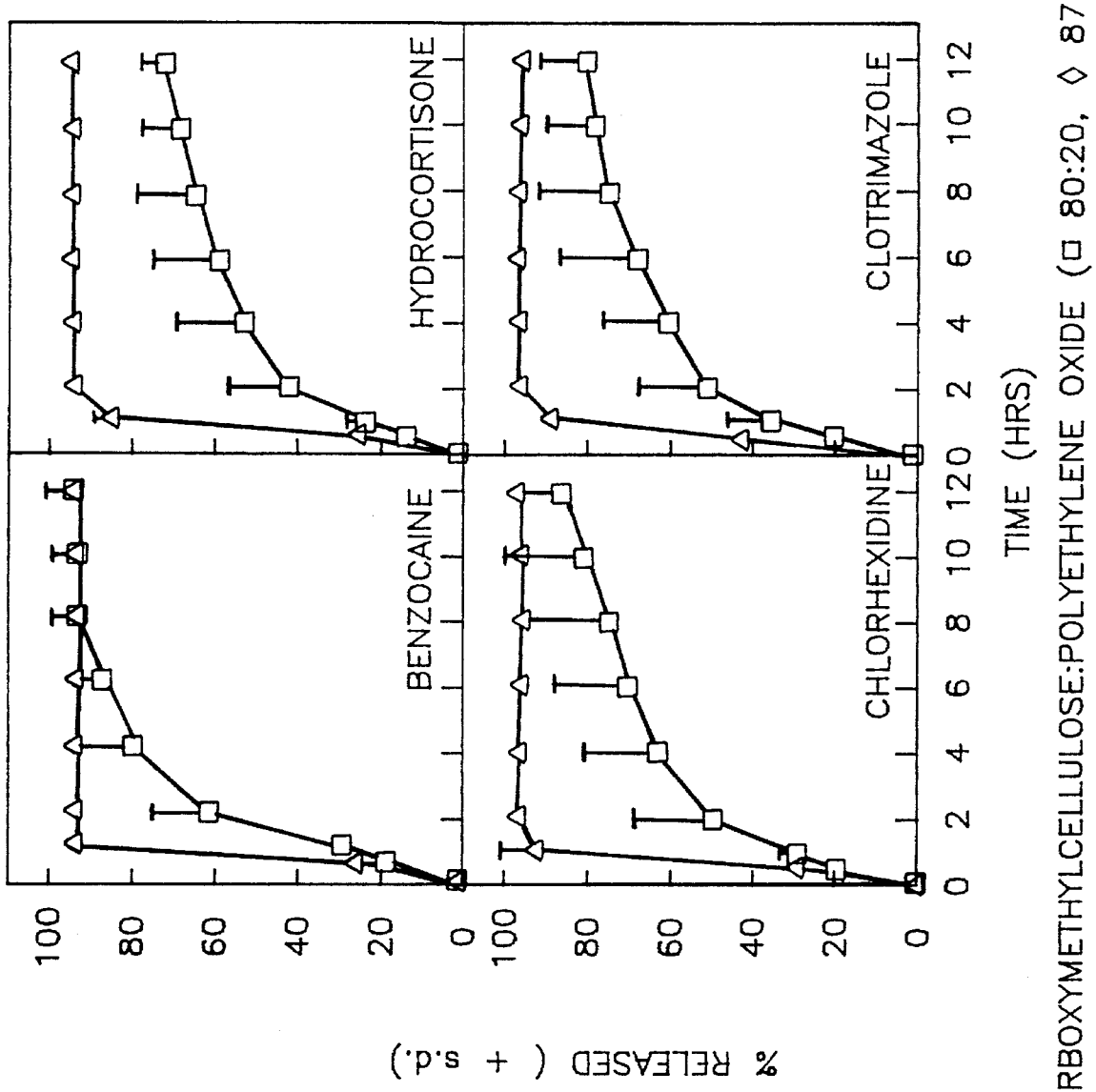
FIG. 12 are graphs showing release profiles (percent released [+s.d.]) vs. time (in hours) of four pharmaceuticals from tablets prepared using sodium carboxymethyl cellulose:polyethylene oxide combinations.
Figure 13:
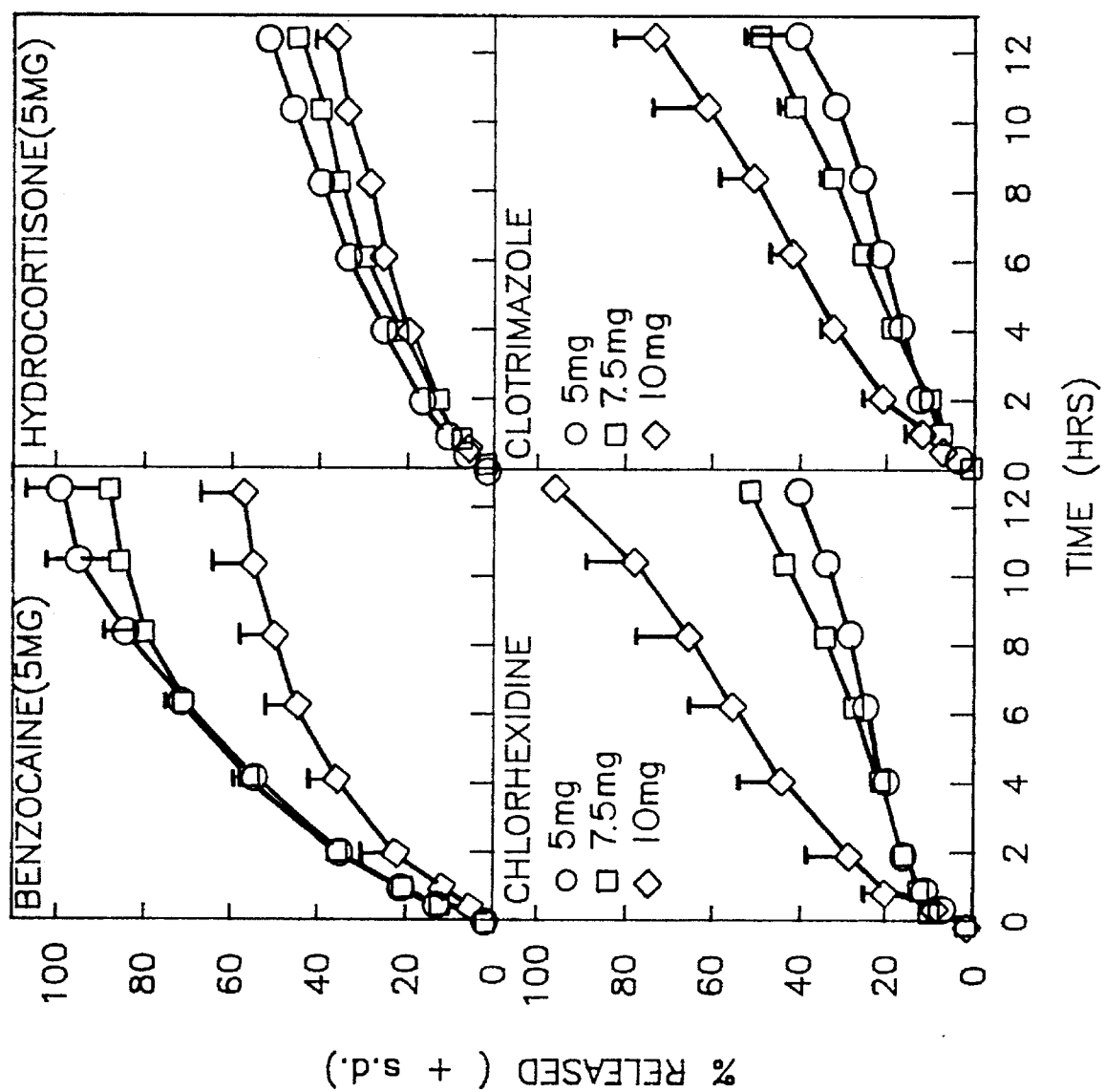
FIG. 13 are graphs showing percent released (+s.d.) of the named pharmaceuticals from tablets made using a combination of sodium carboxymethyl cellulose and polyethylene oxide as shown at the different loading levels of pharmaceuticals as shown. [Loading levels of benzocaine and hydrocortisone were kept constant.]
Figures 14A, 14B:
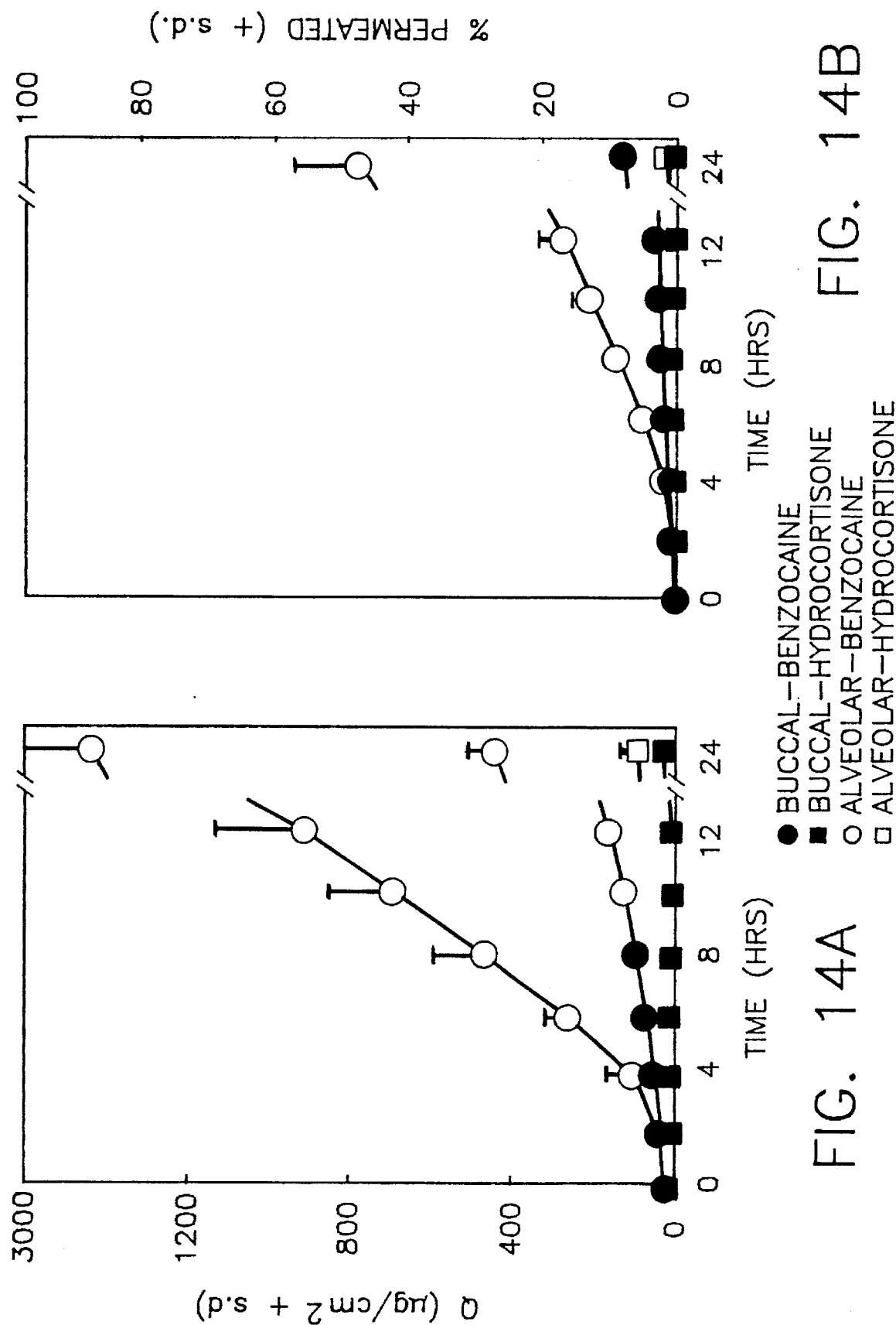
FIGS. 14-A and 14-B are graphs showing a cumulative transmucosal permeation profiles of benzocaine and hydrocortisone from tablets prepared from a combination of sodium carboxymethyl cellulose:polyethylene oxide (85:15).

The stability profile of the drugs in isotonic phosphate buffer containing 40% PEG 400 is shown in FIG. 3. As can be seen, all the four drugs were stable over the 48-hour study period.

EXAMPLE 1

The following pharmaceuticals are used in making the dosage units of this Example: clotrimazole, chlorhexidine (diacetate salt), benzocaine and hydrocortisone. They are obtained from Sigma Chemical Co. (St. Louis, Mo.). The following mucoadhesive polymers are used: sodium carboxymethyl cellulose 7H3SF is obtained from Aqualon (Wilmington, Del.), Carbopol 974P from BF Goodrich (Breckville, Ohio), polyethylene oxide (MW 4,000,000) and polyvinylmethyl-ether/maleic anhydride (MN 67,000) from Polysciences (Warrington, Pa.) and gum tragacanth from Sigma Chemical Co. (St. Louis, Mo.). The backing material used is a laminate sold under the designation Scotchpack, sold by 3M Corporation (St. Paul, Minn.).

The following additional materials are all obtained from Fisher Scientific (Fair Lawn, N.J.): talc and methanol. The dosage units are prepared as follows. The mucoadhesive polymer (1 percent w/w) is first dispersed in glycerol (1 percent w/w). Glycerol is used as a plasticizer. Stock solution of the active ingredients is made in methanol and the amount required to obtain the desired loading (2 mg/gm of polymer solution, in the case of benzocaine and hydrocortisone, and 1 mg/gm in the case of chlorhexidine and clotrimazole) is added to the polymeric dispersion. A required amount of water is then added to the dispersion to make up to 100 percent and the resultant mucilage is thoroughly stirred. The mucilage mixture is cast on the backing laminate material Scotchpack to a wet thickness of 1,000 micrometers, using a laboratory coating machine (Warner-Mathis/Zurich, Switzerland). After proper drying, the dosage units are cut into circular shapes (9 mm diameter). They are assayed for content of pharmaceutical and for pharmaceutical release from the dosage units.

Dosage units made are exemplified in the FIGURES of the Application.

EXAMPLE 2

Dosage units in the form of tablets are prepared using a tablet press (Stokes/Menomonee Falls, Wis.) with a compression force of 10,000–11,000 lbs (~5 metric tons) for 5 sec. The diameter of the die cavity is 8 mm and 100 mg of the tablet mixture is used. Clotrimazole, chlorhexidine, benzocaine and hydrocortisone are each weighed at a 5% (w/w) level. Talc, as a lubricant and glidant, is also added at 5% (w/w) level to the tablet mixture. The four therapeutic agents and talc account for a total of 25% (w/w) of the tablet mixture, with the remaining 75% being mucoadhesive polymer(s). The mucoadhesive polymers and combinations described in Example 1 are used. The tablet mixtures are mixed well prior to compression to form tablets.

To determine the effect of increasing the loading of antifungal agents on pharmaceutical release profiles, in addition to the 5% loading, two additional loading levels are tried. Chlorhexidine and clotrimazole are each added at a level of 7.5% and 10% respectively in the two batches of tablets made, while the loadings of benzocaine and hydrocortisone are maintained at 5% in both the batches. The polymer combination of sodium carboxymethyl cellulose-:polyethylene oxide (80:20) was used, with the total polymer content being 70% and 65% in the two batches, respectively.

What is claimed is:

1. A mucosal adhesive dosage unit adapted to use for treatment of oral cavity infection selected from a) the forms consisting of a dosage unit wherein mucoadhesive polymer layer having intermixed pharmaceuticals is adhered to a protective backing layer, and b) a tablet comprising a mucosal adhesive polymer mixture having intermixed pharmaceuticals;

said mucosal adhesive dosage unit adhering to the oral mucosal tissue for at least about 12 hours, said mucosal adhesive dosage unit having a therapeutic dosage amount of one or more antimicrobial agents and one or more anti-inflammatory agents, said dosage unit releasing the antimicrobial agent and anti-inflammatory agent at a substantially constant rate for at least 12 hours to treat infection in the oral mucosa.

2. A dosage unit of claim 1 wherein the dosage unit further comprises a therapeutic amount of one or more local anesthetics which are released at a sufficient rate to reduce any pain of the subject treated at the site of treatment.

3. A dosage unit of claim 1 wherein the one or more antimicrobial agents are one or more antifungal agents.

4. A dosage unit of claim 3 wherein the one or more antifungal agents is chlorhexidine or clotrimazole or consists of 20–80 percent by weight of chlorhexidine and 20–80 percent by weight of clotrimazole.

5. A dosage unit of claim 4 wherein the anti-inflammatory agent is hydrocortisone.

6. A dosage unit of claim 2 wherein the local anesthetic is benzocaine.

7. A dosage unit of claim 2 wherein the one or more antimicrobial agents are selected from the group consisting of chlorhexidine or clotrimazole or consists of 20–80 percent by weight of chlorhexidine and 20–80 percent by weight of clotrimazole.

8. A dosage unit of claim 2 wherein the antimicrobial agent is chlorhexidine or clotrimazole or consists of 20–80 percent by weight of chlorhexidine and 20–80 percent by weight of clotrimazole, the anti-inflammatory agent is hydrocortisone, and the local anesthetic is benzocaine.

* * * * *